(12) United States Patent
Morin et al.

(10) Patent No.: US 11,833,273 B2
(45) Date of Patent: Dec. 5, 2023

(54) LEAFLET THICKNESS VIA STRETCHING TECHNIQUES FOR IMPROVED VALVE DURABILITY

(71) Applicant: St. Jude Medical, Cardiology Division, Inc., St. Paul, MN (US)

(72) Inventors: Kristen T. Morin, St. Paul, MN (US); Jay Reimer, Saint Paul, MN (US); Keith T. High, White Bear Lake, MN (US); Kristopher Henry Vietmeier, Monticello, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 257 days.

(21) Appl. No.: 17/231,628

(22) Filed: Apr. 15, 2021

(65) Prior Publication Data

US 2021/0322649 A1 Oct. 21, 2021

Related U.S. Application Data

(60) Provisional application No. 63/010,819, filed on Apr. 16, 2020.

(51) Int. Cl.
| | | |
|---|---|---|
| *A61F 2/24* | (2006.01) | |
| *A61L 27/54* | (2006.01) | |
| *A61L 27/36* | (2006.01) | |
| *A61L 27/38* | (2006.01) | |
| *B29C 59/02* | (2006.01) | |

(52) U.S. Cl.
CPC ............ *A61L 27/54* (2013.01); *A61F 2/2415* (2013.01); *A61F 2/2418* (2013.01); *A61L 27/3687* (2013.01); *A61L 27/3826* (2013.01); *A61L 27/3834* (2013.01); *B29C 59/02* (2013.01); *A61F 2240/004* (2013.01); *A61L 2300/252* (2013.01); *A61L 2430/20* (2013.01)

(58) Field of Classification Search
CPC ........ A61F 2/24; A61F 2/2415; A61F 2/2418; A61L 27/3687; A61L 2430/20; B29C 59/02

See application file for complete search history.

(56) References Cited

U.S. PATENT DOCUMENTS

| | | | | |
|---|---|---|---|---|
| 6,378,221 | B1 * | 4/2002 | Ekholm, Jr. ......... | G01B 11/245 33/551 |
| 7,208,000 | B2 * | 4/2007 | Love ..................... | A61F 2/2415 30/360 |
| 9,498,287 | B2 | 11/2016 | Tian et al. | |
| 11,517,427 | B2 * | 12/2022 | Nguyen ................ | A61F 2/2415 |
| 2002/0157271 | A1 * | 10/2002 | Ekholm, Jr. ........... | G01B 21/08 33/551 |

(Continued)

OTHER PUBLICATIONS

International Search Report includng Written Opinion for PCT/US2021/027476 dated Aug. 9, 2021; 17 pages.

*Primary Examiner* — Suzette J Gherbi
(74) *Attorney, Agent, or Firm* — SLEMAN & LUND LLP

(57) ABSTRACT

A prosthetic heart valve includes a support structure and a valve assembly disposed within the support structure, the valve assembly including a plurality of leaflets. Each leaflet includes a sewing edge and a free edge. The leaflet is formed from a sheet of leaflet material which is processed so that the resulting leaflet has a non-uniform thickness. Various methods may be used to form the leaflet with a non-uniform thickness.

8 Claims, 8 Drawing Sheets

(56) References Cited

U.S. PATENT DOCUMENTS

2005/0209588 A1* 9/2005 Larson .................... A61N 7/02
 607/96
2014/0257472 A1 9/2014 Kutty et al.
2017/0209262 A1 7/2017 McKinley et al.
2017/0209263 A1 7/2017 Munnelly et al.

* cited by examiner

LEAFLET THICKNESS VIA STRETCHING TECHNIQUES FOR IMPROVED VALVE DURABILITY

CROSS-REFERENCE TO RELATED APPLICATIONS

The present application claims the benefit of the filing date of U.S. Provisional Patent Application No. 63/010,819, filed Apr. 16, 2020, the disclosure of which is hereby incorporated by reference herein.

BACKGROUND OF THE DISCLOSURE

This disclosure relates to prosthetic heart valves, and more particularly to prosthetic heart valves that can be collapsed to a relatively small size for delivery into a patient and then re-expanded to full operating size at the final implant site in the patient. More particularly, this disclosure relates to methods for processing the tissue used for the valve components in such prosthetic heart valves.

Prosthetic heart valves, including surgical heart valves and collapsible heart valves intended for transcatheter aortic valve replacement/repair ("TAVR") or transcatheter mitral valve replacement/repair ("TMVR"), are well known in the patent literature. Surgical or mechanical heart valves may be sutured into a native annulus of a patient during an open-heart surgical procedure, for example. Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

Leaflets, cuffs and valve assemblies for prosthetic heart valves may be derived from various natural tissues, including various animal tissues, or may be a combination of natural tissues. Typically prior to implantation, the biological tissue is chemically cross-linked or fixed with agents, such as glutaraldehyde or formaldehyde, in order to prevent rejection when implanted in a recipient, to provide sterilization, and to help stabilize the proteins in the tissue, thereby making the tissue and the prosthetic valve containing such tissue more durable and able to withstand prolonged use, including millions of cycles of opening and closing under circulatory pressure without fatigue. Glutaraldehyde is the most commonly used fixative that can be applied at a physiological pH under aqueous conditions to prepare the tissue for implantation.

However, there is variability within natural tissue that can lead to challenges in properly selecting and manufacturing such heart valves and leaflets. Leaflets made from animal tissue have been shown to calcify to varying degrees in clinical use, limiting their lifespans. Over an extended patient lifespan, such biological leaflets may eventually erode or tear, creating a need for further surgical intervention or an additional valve replacement.

Additionally, the thickness of the leaflet material is important due to the growing prevalence of transcatheter heart valves including TAVR and TMVR. Thinner materials enable the prosthetic heart valve to be collapsed to a smaller size for delivery to the patient's heart percutaneously.

Therefore, there is a need for further improvements to leaflet materials to address the current shortcomings of leaflets made from animal tissue. A preferred material for use in prosthetic heart valve leaflets will be resistant to calcification and have a long functional life. Among other advantages, the present invention may address one or more of these needs

BRIEF SUMMARY OF THE DISCLOSURE

In accordance with certain possible aspects of the disclosure, a prosthetic heart valve may include a support structure, and a valve assembly disposed within the support structure. The valve assembly may include a plurality of leaflets. Each of the leaflets may have a sewing edge and a free edge, may be formed from a sheet of tissue, and may have a non-uniform thickness. Each of the leaflets may have a plurality of regions, and each of the regions may have a different thickness. The thickness of a first region of the leaflet may be between about 5% and about 20% less than the thickness of a second region of the leaflet. The sewing edge may have a thickness between about 10% and about 20% greater than a thickness of the free edge. The thickness of the leaflet may be greater at the sewing edge and gradually decreases toward the free edge. The thickness of the leaflet may decrease with a smooth transition from the sewing edge to the free edge, or with a stepped transition from the sewing edge to the free edge. Collagen-producing cells may be incorporated into the tissue. The collagen-producing cells may be smooth-muscle cells, fibroblasts or stem cells. The collagen-producing cells may be incubated on the tissue so as to produce collagen on the tissue.

An additional embodiment of the present disclosure provides a method for fabricating a leaflet for a prosthetic heart valve, the leaflet having a non-uniform thickness. The method includes providing a sheet of a leaflet material, the sheet having a first thickness, and attaching the sheet to a frame. A first probe may be moved into contact with a surface of the sheet, whereupon the probe may exert a force in a region of the sheet to change the thickness of that region to a second thickness different from the first thickness. The second thickness may be less than the first thickness. The first thickness may be about 100 μm and the second thickness may be about 75 μm. The first probe may contact a top surface of the sheet, and the method may also include moving a second probe into contact with a bottom surface of the sheet, whereupon the first probe and the second probe may collectively exert a compressive force on the region of the sheet which may decrease the thickness of the region. The method may also form a plurality of ribs throughout the sheet. The sheet may be tissue and the tissue may be fixed with glutaraldehyde.

In another embodiment of the present disclosure, a method for fabricating a leaflet for a prosthetic heart valve may include layering a sheet of a leaflet material over a first mold portion having a first leaflet form, the sheet having a uniform thickness; and applying a second mold portion to the sheet, the second mold portion having a second leaflet form different from the first leaflet form. The second mold portion may push the sheet against the first leaflet form to form the sheet into a sheet having a non-uniform thickness. The leaflet material may be tissue, and the tissue may be fixed.

In an additional embodiment of the disclosure, a method for fabricating a leaflet for a prosthetic heart valve may include providing a sheet having a first major surface, a second major surface, and a first thickness between the first major surface and the second major surface; positioning a first plate adjacent to the first major surface and a second plate adjacent to the second major surface so that a distance between the first plate and the second plate defines a desired sheet thickness greater than the first thickness; and moving opposed edges of the sheet toward one another between the first plate and the second plate to force the sheet against the first plate and the second plate to increase the thickness of the sheet to the desired thickness. The first plate and the second plate may be parallel. The first plate and the second plate may not be parallel, the first plate may have a first edge and a second edge opposite the first edge, and the second plate may have a first plate edge and a second plate edge opposite the first plate edge. The distance between the first edge of the first plate and the first plate edge of the second plate may be less than the distance between the second edge of the first plate and the second plate edge of the second plate.

Further features of the invention, its nature and various advantages, will be more apparent from the accompanying drawings and the following detailed description.

BRIEF DESCRIPTION OF THE DRAWINGS

This disclosure may be best understood by reference to the following description taken in conjunction with the accompanying drawing figures, in which.

DETAILED DESCRIPTION

As used herein, the term "inflow," when used in connection with a prosthetic heart valve, refers to the end of the heart valve through which blood enters when the valve is functioning as intended, whereas the term "outflow," when used in connection with a prosthetic heart valve, refers to the end of the heart valve through which blood exits when the valve is functioning as intended. Also as used herein, the terms "generally," "substantially," "approximately," and "about" are intended to mean that slight deviations from absolute are included within the scope of the term so modified. When used to indicate relative locations within the prosthetic heart valve, the terms "longitudinal" and "vertical" are to be taken as the direction of the axis extending between the inflow end and the outflow end of the stent of the heart valve, along the direction of intended blood flow; the term "flow direction" is to be taken as the direction from the inflow end to the outflow end of the stent of the heart valve; and the terms "above," "below," "high," and "low" are to be taken as relative to the inflow end of the stent. "Above" and "high" are to be understood as relatively farther from the inflow end of the stent in the direction of intended blood flow, and "below" and "low" are to be understood as relatively closer to the inflow end of the stent in the direction of intended blood flow. When used to indicate relative locations within the prosthetic heart valve, the term "circumferential" is to be taken as the direction of rotation about the longitudinal axis of the stent.

Figure 1:
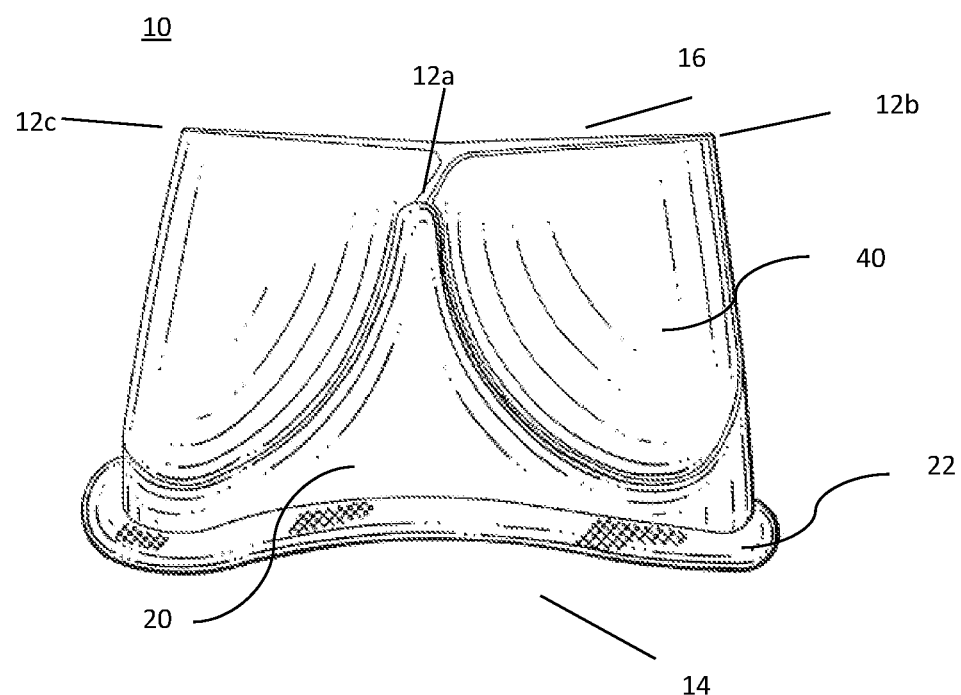
FIG. 1 is a perspective view of a surgical heart valve according to the prior art.

An illustrative embodiment of a surgical heart valve 10 ("SHV") is shown in FIG. 1. SHV 10 may be surgically implanted into a patient to replace a native heart valve that may be malfunctioning, such as the aortic valve, mitral valve, pulmonary valve or the tricuspid valve. The SHV 10 may be sutured into a native valve annulus, such as during an open-heart surgical procedure. The SHV 10 may have a non-collapsible frame (not shown) having a generally annular shape. The frame is typically made from a biologically compatible metal, such as titanium, Elgiloy®, or MP35N, or a biologically compatible polymer, such as PEEK or acetal. Since the valve of the illustrative embodiment is a tricuspid valve (e.g., for use in replacing a patient's aortic valve), the frame has three commissure posts 12a, 12b and 12c that are equally spaced from one another around the circumference of the frame. Each commissure post stands up from the annularly continuous base of the frame. The commissure posts 12a-c may support and/or serve as attachment points for a plurality of prosthetic leaflets (not shown). Although the frame is shown with three commissure posts 12a-c for supporting a three-leaflet valve assembly, it should be understood that the stent could include more or fewer commissure posts for supporting a corresponding number of prosthetic leaflets. The base of the frame may include a blood-inflow edge portion 14 that is scalloped as one proceeds around the frame to approximately match the natural scallop of the native valve annulus. The frame also includes an annularly continuous blood-outflow edge portion 16, which merges with and becomes part of each commissure post 12. The inflow edge portion 14, outflow edge portion 16 and flexibility of the frame are designed to help insure proper opening and coaptation of the valve leaflets of the prosthetic heart valve during use.

The frame may be covered by a fabric covering (not shown), particularly over each commissure post 12. One example of an appropriate covering of the fabric is reemay fabric, which is a spun form of polyester. A ring 20, such as a silicone ring, may be positioned around the outside of the inflow edge portion 14. The entire frame and ring 20 may be completely covered inside and out by a further fabric layer. Subsequently, a layer of tissue 22 may be applied over the fabric layer, including both inside and outside of the frame and over the ring 20. Tissue layer 22 may be formed of any mammalian tissue, and in particular any mammalian pericardium tissue, such as porcine, equine or bovine pericardium. In the completed SHV 10, the covered ring 20 serves as a sewing cuff for sewing the prosthetic heart valve into the native valve annulus of the patient.

Figure 2:
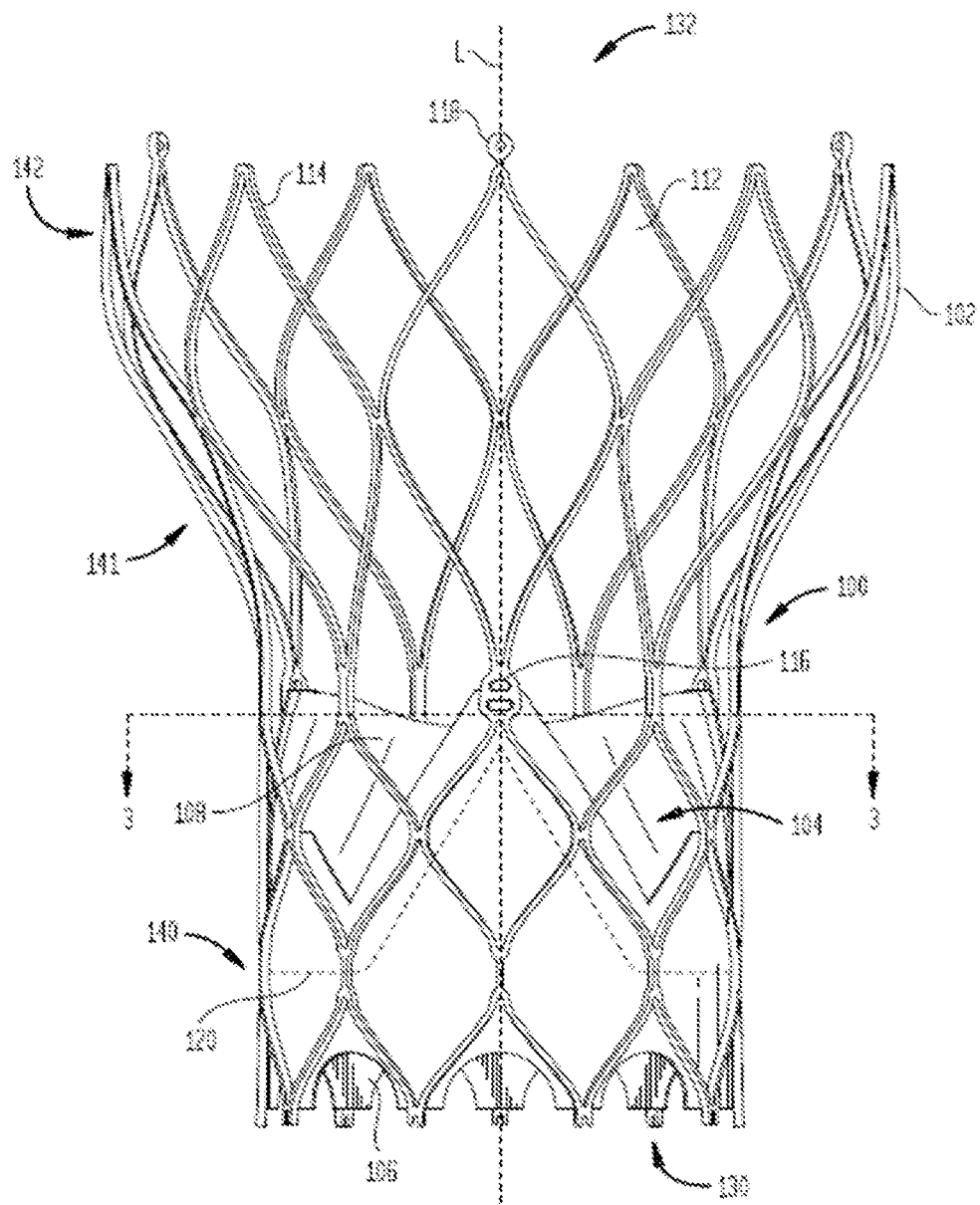
FIG. 2 is a side view of a collapsible stent-supported prosthetic heart valve according to the prior art, in an expanded condition.

FIG. 2 shows one embodiment of an expandable (and optionally collapsible) stent-supported prosthetic heart valve 100 according to the prior art, the prosthetic heart valve being shown in an expanded condition. Prosthetic heart valve 100 is designed to replace the function of the native aortic valve of a patient, and includes a stent 102 which serves as a frame for the valve elements. Stent 102 extends along a lengthwise or longitudinal axis L from an inflow or annulus end 130 to an outflow or aortic end 132, and includes an annulus section 140 adjacent inflow end 130 and an aortic section 142 adjacent outflow end 132. Annulus section 140 may be in the form of a cylinder having a substantially constant diameter along its length, and may have a relatively small transverse cross-section in the expanded condition in comparison to the transverse cross-section of aortic section 142. A transition section 141 may taper outwardly from annulus section 140 to aortic section 142. Each of the sections of stent 102 includes a plurality of cells 112 formed by interconnected struts 114. Each cell 112 may include four struts 114 connected together generally in a diamond shape so as to form a cell that may be readily collapsed and expanded. It will be appreciated that a smaller or larger number of struts may be used to form cells having a different shape. The cells 112 in each section of stent 102 may be connected to one another in one or more annular rows around the stent. For example, as shown in FIG. 2, annulus section 140 may have two annular rows of complete cells 112, with the cells in one annular row offset by one-half cell width in the circumferential direction from the cells in the other annular row. Aortic section 142 and transition section 141 may each have one or more annular rows of complete or partial cells 112. The cells in aortic section 142 may be larger than the cells in annulus section 140 so as to better enable prosthetic valve 100 to be positioned within the aortic annulus without the structure of stent 102 interfering with blood flow to the coronary arteries. At least partly due to the shape of cells 112, stent 102 elongates in the direction of longitudinal axis L as the cells collapse when the stent transitions from the expanded condition to the collapsed condition, and shortens in the direction of longitudinal axis L as the stent transitions from the collapsed condition to the expanded condition.

Stent 102 may include one or more retaining elements 118 at outflow end 132, the retaining elements being sized and shaped to cooperate with retaining structures provided on a deployment device (not shown). Stent 102 may also include a plurality of commissure attachment features 116 for mounting the leaflet commissures of the valve assembly to the stent. As can be seen in FIG. 2, each commissure attachment feature 116 may lie at the intersection of four cells 112, two of the cells being adjacent one another in the same annular row, and the other two cells being in different annular rows and lying in end-to-end relationship. Commissure attachment features 116 may be positioned entirely within annulus section 140 or at the juncture of annulus section 140 and transition section 141, and may include one or more eyelets or apertures which facilitate the suturing of the leaflet commissures to stent 102. Stent 102 may be formed as a unitary structure, for example, by laser cutting or etching a tube of a superelastic and/or shape-memory metal alloy, such as a nickel-titanium alloy of the type sold under the designation nitinol. It should be understood that stent 102 may include other forms of commissure attachment features, or may omit commissure attachment features 116, with the prosthetic leaflets being attached to the stent via other mechanisms, such as direct suturing or via intermediary attachment panels.

Prosthetic heart valve 100 includes a valve assembly 104 which may be positioned entirely in the annulus section 140 of stent 102. Valve assembly 104 includes a plurality of leaflets 108 that collectively function as a one-way valve by coapting with one another, and a cuff 106 positioned on the luminal surface of stent 102 surrounding leaflets 108. Although cuff 106 is shown in FIG. 2 as being disposed on the luminal or inner surface of annulus section 140, the cuff may be disposed on the abluminal or outer surface of the annulus section, or may cover all or part of either or both of the luminal and abluminal surfaces of the annulus section. As prosthetic heart valve 100 is intended to replace the aortic valve (which ordinarily is a tri-leaflet valve), it is shown in FIG. 2 with three leaflets 108.

Figure 3:
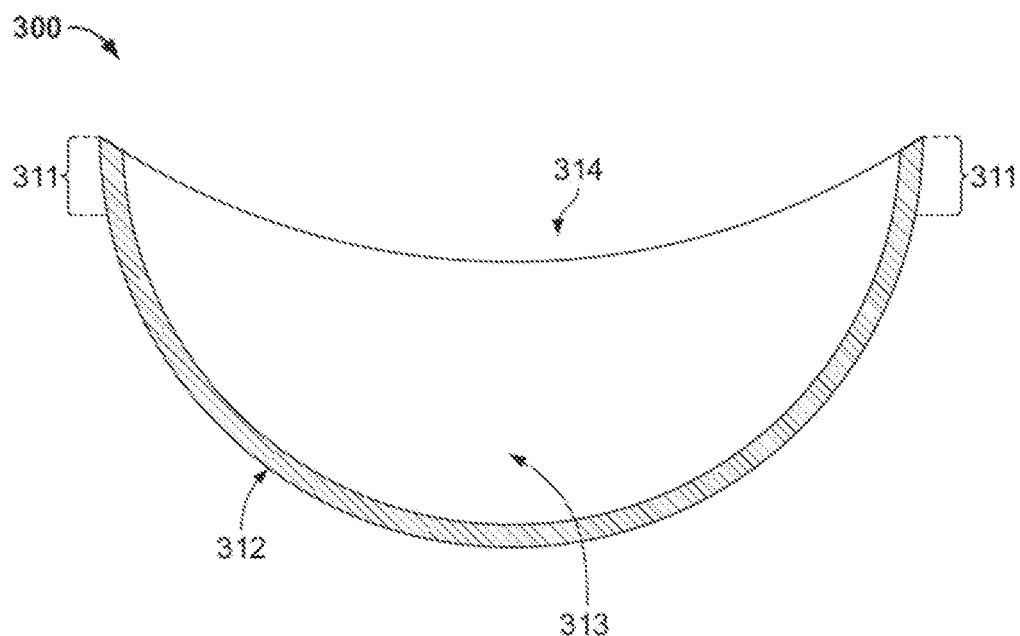
FIG. 3 is a highly schematic illustration of a leaflet, identifying the pertinent regions of the leaflet.

FIG. 3 is a schematic drawing of a leaflet 108 and the pertinent regions of the leaflet as are known in the art. The leaflet 108 includes regions 120 that form commissures with adjacent leaflets, a sewing edge 122, a belly 124 and a free edge 126. The commissure regions 120 represent high stress regions of the leaflet at which the leaflet may be mounted to the support structure of the prosthetic heart valve, such as commissure attachment features 116 of prosthetic heart valve 100. Between the leaflet commissures 120, each leaflet 108 may be sutured to stent 102 and/or to cuff 106 along sewing edge 122, indicated with broken lines in FIG. 2. Leaflets 108 may be joined to stent 102 and/or to cuff 106 by techniques known in the art other than suturing. Above belly 124, leaflets 108 are free to move radially inward to coapt with one another along their free edges 126. When prosthetic heart valve 100 is implanted in the native aortic valve annulus, blood flows in an antegrade direction from inflow end 130, past leaflets 108, and toward outflow end 132. This occurs when the pressure in the left ventricle is greater than the pressure in the aorta, forcing leaflets 108 to open. When the pressure in the aorta is greater than the pressure in the left ventricle, leaflets 108 are forced closed and coapt with one another along their free edges, blocking blood from flowing through prosthetic heart valve 100 in a retrograde direction from outflow end 132 to inflow end 130, which allows the left and right coronary arteries to fill and feed blood to the heart muscle. It will be appreciated that prosthetic heart valves according to aspects of the present disclosure may have more or less than the three leaflets 108 and commissure attachment features 116 shown in FIG. 2 and described above.

In operation, prosthetic heart valve 100 may be used to replace a native heart valve, such as the aortic valve; a surgical heart valve; or a heart valve that has undergone a surgical procedure. Prosthetic heart valve 100 may be delivered to the desired site (e.g., near the native aortic annulus) using any suitable delivery device (not shown). During delivery, prosthetic heart valve 100 is disposed inside the delivery device in the collapsed condition. The delivery device may be introduced into the patient using any known percutaneous procedure, such as a transfemoral, transapical, transvenous, or transseptal delivery procedure. Once the delivery device has reached the target site, the user may deploy prosthetic heart valve 100. Upon deployment, prosthetic heart valve 100 expands into secure engagement within the native aortic annulus. When prosthetic heart valve 100 is properly positioned inside the heart, it works as a one-way valve, allowing blood to flow in one direction and preventing blood from flowing in the opposite direction.

The descriptions of surgical heart valve 10 and collapsible prosthetic heart valve 100 are for context only. Thus, the leaflet materials described herein may be used in surgical heart valves that are similar to surgical heart valve 10 or surgical heart valves that are very different therefrom. Similarly, the presently disclosed leaflet materials may be used in collapsible prosthetic heart valves that are similar to prosthetic heart valve 100, or prosthetic heart valves that are very different therefrom, such as heart valves having a balloon-expandable stent, heart valves that do not have an aortic section, heart valves intended to replace other cardiac valves, such as the mitral valve, etc. Therefore, the descriptions herein of surgical heart valve 10 and collapsible prosthetic heart valve 100 should in no way be considered as limiting the features and applications of the leaflet structures disclosed herein.

Prosthetic heart valves may be made with at least some tissue of biological origin. "Biological tissue" or "tissue," as used herein, refers to biological tissue dissected from an animal, typically a mammalian species, for example, human, bovine, porcine, or canine. Porcine tissue and bovine tissue are routinely used in bioprosthetic devices. Specific tissue types that may be used include, without limitation, any blood vessel, pericardial tissue, heart muscle tissue, dura matter and the like. More than one species and tissue type may be used in a valve assembly. "Fixed" or "cross-linked" tissue refers to tissue in which the proteins have reduced solubility, antigenicity, and biodegradability as compared to the proteins in the native tissue. "Fixing" or "cross-linking" can be accomplished by a number of techniques, for example, by treatment with aldehydes, epoxides, carbodimides or genipin, or by photo fixation. Conventionally, fixing can be performed by cross-linking the amine groups of the tissue proteins with an aldehyde, such as a solution of about 0.001 v/v % to about 5 v/v % of glutaraldehyde or formaldehyde.

Figure 4A:
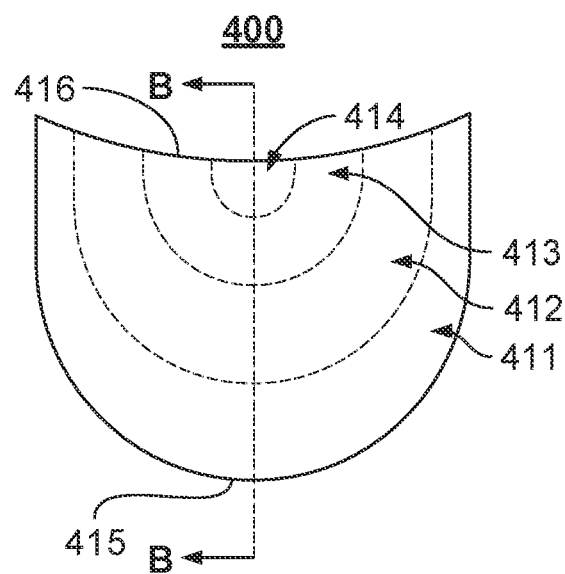
FIG. 4A is a plan view of an embodiment of a leaflet of the present disclosure.

FIG. 4A is a plan view of an embodiment of a leaflet 400 according to the present disclosure. Leaflet 400 may be formed of any material that may be elastic, including but not limited to, polymers, fibers or tissue. The polymers may include ultrahigh molecular weight polyethylene, polyester, or other polymers such as PEEK or acetal. The tissue may include biological tissue, such as porcine pericardium, bovine pericardium, bovine or porcine native leaflet cusps, or other mammalian tissue. The leaflet may also be formed from sheets of a shape-memory metal, such as nitinol. The leaflet 400 includes a free edge 416, a sewing edge 418 and a belly 415 therebetween, and may have a non-uniform thickness such that the leaflet thickness may be greater near the sewing edge 418, and may gradually decrease towards the free edge 416. Having a greater thickness near the sewing edge may provide greater strength for sewing the leaflet to the cuff and/or stent or frame and for resisting the strain at the sewing edge when the leaflet opens and closes. Having less thickness near the free edge may result in less mass in this portion of the leaflet that moves the most, making it easier for the leaflet to open and close. More particularly, the leaflet 400 may include at least two regions of different thicknesses, as denoted by dashed lines in FIG. 4A. FIG. 4A shows one embodiment in which the leaflet 400 includes multiple regions of different thicknesses. A first region 411 of the leaflet may have a thickness between about 15 µm and about 750 µm. The thickness of the leaflet may change by between about 5% and about 20% between each region. Thus, the thickness of a second region 412 may be about 5% less than the thickness of the first region 411, the thickness of a third region 413 may be about 5% less than the thickness of the second region 412, and the thickness of a fourth region 414 may be about 5% less than the thickness of the third region 413. The fourth region 414 may have the smallest thickness as compared to the first, second and third regions 411, 412, 413, while the first region 411 may have the greatest thickness as compared to the second, third and fourth regions 412, 413, 414.

Figure 4B:
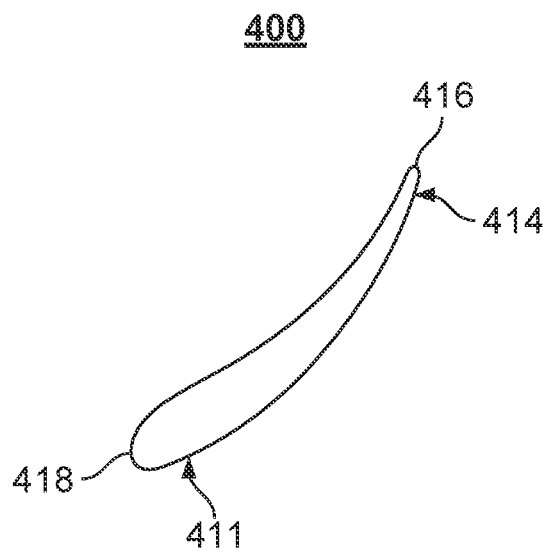
FIG. 4B is a cross-section of an embodiment of the leaflet in accordance with the present disclosure.
Figure 4C:
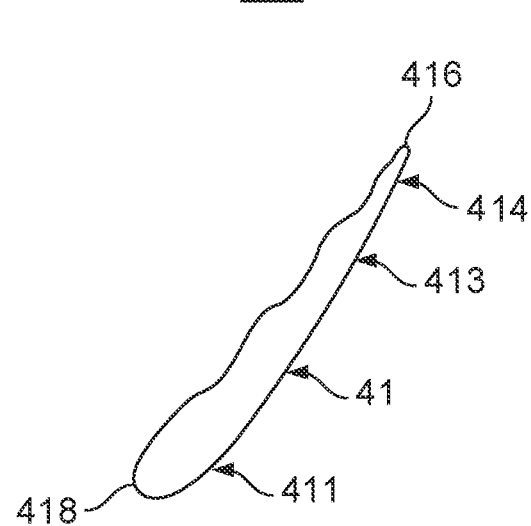
FIG. 4C is a cross-section of another embodiment of the leaflet in accordance with the present disclosure.

FIG. 4B is a transverse cross-section of the leaflet 400 taken along line B-B of FIG. 4A. In one embodiment, shown in FIG. 4B, the thickness of leaflet 400 may gradually decrease from the sewing edge 418 to the free edge 416, creating a smooth transition between regions 411, 412, 413 and 414. FIG. 4C is also a transverse cross-section of the leaflet 400 taken along line B-B of FIG. 4A. In another embodiment, shown in FIG. 4C, the thickness transition between the different regions of the leaflet 400 may be more abrupt, similar to the steps of a staircase. The leaflet 400 may have a region of greatest thickness 411 near the sewing edge 418, a region 412 that is thinner than region 411 by about 5%, a region 413 that is thinner than region 412 by about 5%, and a region 414 that is thinner than region 413 by about 5%. The thickness of each region may vary depending on the function of the region.

Figure 5:
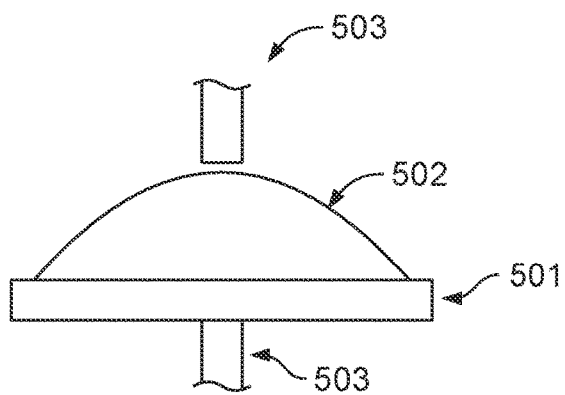
FIG. 5 is a highly schematic representation of a stretching and/or compressing technique according to an embodiment of the present disclosure.

Several techniques are available for changing the thickness across the leaflet. The thickness may be changed by various stretching and compressing techniques. In some embodiments, a sheet 502 of a leaflet material may be stretched or compressed using a probe, as shown in FIG. 5. The sheet 502 may be formed of one or more polymers or tissue. Certain embodiments of the present disclosure will be described in connection with a sheet composed of tissue, but that is not intended to limit the disclosure. In FIG. 5, a sheet 502 of tissue for forming leaflets may be attached to a frame 501. The frame 501 is different from the stent or frame of the prosthetic heart valve. The sheet 502 may be attached to frame 501 by using pins, sutures or barbs, or may be attached by suctioning, gluing, heat bonding or compression from a fixture. The sheet 502 may have an initial thickness of between about 50 µm and about 1000 µm before stretching or compressing. After the sheet 502 has been attached to the frame 501, and with the frame held in a fixed position, one or more probes 503 may be pushed against a bottom surface of the sheet or against a top surface of the sheet to stretch the sheet, or may be pushed against both the bottom and top surfaces of the sheet to compress the sheet. If one probe 503 is pushed against the top surface or against the bottom surface of the sheet 502, the applied force stretches the sheet 502 until a desired thickness is achieved. If probes 503 are pushed against both the top surface and the bottom surface of the sheet 502, the sheet may be compressed between the probes until a desired thickness is achieved. The thickness achieved will depend on the degree of the force applied and the duration of application. The greater the force and the longer it is applied, the thinner sheet 502 can become. The desired thickness may be between about 25 μm and about 500 μm. The probe(s) 503 may be applied to various regions of the sheet 502 with different forces for different times to produce regions of the sheet having different thicknesses.

The sheet 502 may be pre-cut into the shape of a leaflet before the stretching and/or compressing process, or may be cut into a leaflet shape after being stretched and/or compressed. When the sheet 502 is composed of tissue, the sheet may be cut into a leaflet shape before or after fixation, and may be stretched and/or compressed during or after fixation. When stretched and/or compressed after fixation, the sheet of tissue 502 will still retain the regions of different thicknesses. When the sheet of tissue 502 is stretched and/or compressed during fixation, cross-linking may retain the thickness of the stretched and/or compressed sheet. Fixation involves the sheet of tissue 502 being submerged in glutaraldehyde for at least several hours.

Figure 6A:
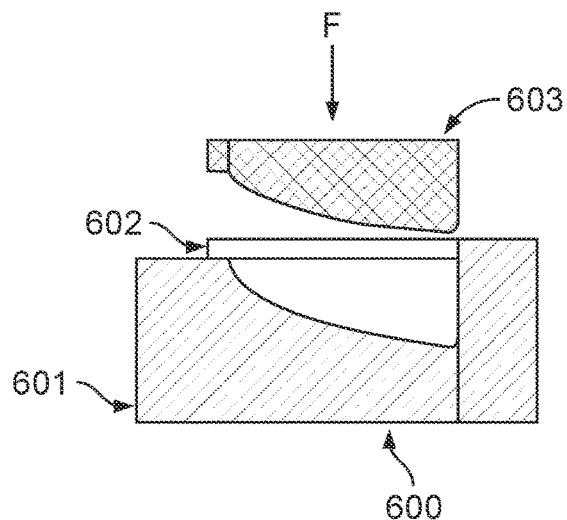
FIG. 6A is a highly schematic representation of a stretching and/or compressing technique according to another embodiment of the present disclosure.
Figure 6B:
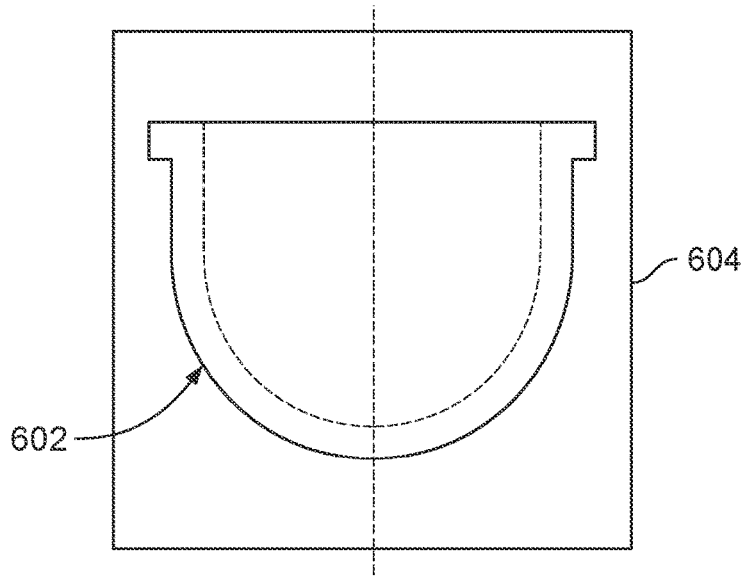
FIG. 6B is a highly schematic representation of a stretching and/or compressing technique according to a further embodiment of the present disclosure.

FIGS. 6A and 6B show another technique for stretching and/or compressing the sheet. In this technique, a sheet 602 of leaflet material may be pre-cut into the shape of a leaflet or may be cut into a leaflet by laser cutting or other known technique. If sheet 602 is composed of tissue, the sheet may undergo fixation, i.e., before or during the stretching and/or compressing process. The sheet 602 may be stretched and/or compressed in various steps using a mold 600. The sheet 602 is first positioned over a shaped cavity in a bottom portion 601 of mold 600. A top portion 603 of the mold is then placed over the top of the sheet 602 and pushed toward the bottom portion, applying a force to the sheet represented by arrow F. The top portion 603 and bottom portion 601 of the mold 600 may be shaped similarly to one another, but not quite complementary. Rather, the top and bottom portions of mold 600 may be designed to produce varying thicknesses in the tissue 602. In FIG. 6B, the sheet 602 is shown inside the bottom portion 601 of the mold 600 after the top portion 603 has been pushed on the top surface of the sheet 602 and then removed. The sheet 602 may remain in the mold 600 for between about 10 minutes and about 48 hours, or more, to achieve the desired thickness and shape.

Figure 7:
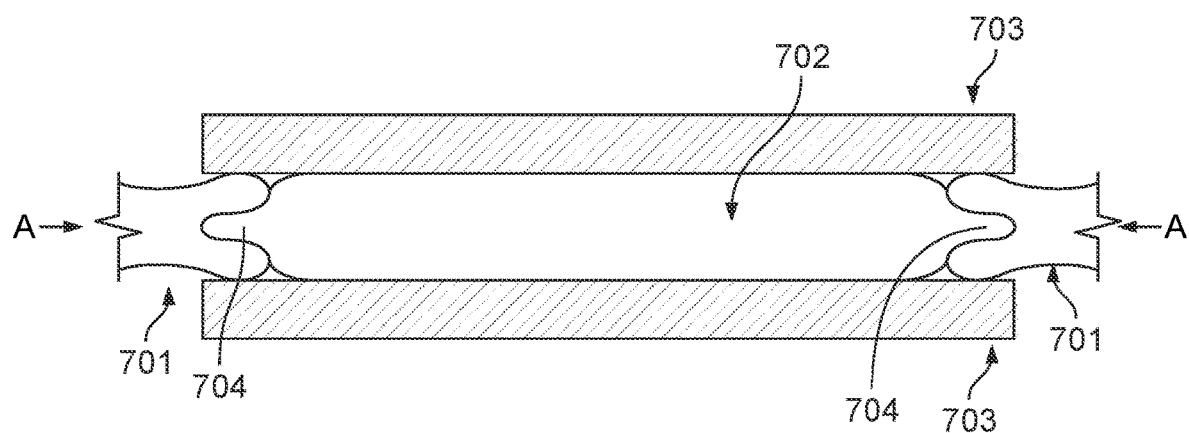
FIG. 7 is a highly schematic representation of a thickening technique according to an embodiment of the present disclosure.

FIG. 7 is an additional embodiment of the sheet as described above, in which one or more regions of the sheet may be compressed. The sheet 702 may be held at its opposite edges 704 by clips 701. Clips 701 may apply a force to push edges 704 of the sheet 702 inward toward one another and toward the center as indicated by arrows A. Plates 703 may be positioned on opposite sides of the sheet 702 and spaced apart from one another by a distance that corresponds to the thickness of the sheet that is desired. The plates 703 may be positioned to be parallel to form a uniform thickness sheet or to be not parallel to form a sheet that is thinner at one edge and thicker at an opposite edge. When the clips 701 are moved toward one another while the plates 703 are held in fixed positions, the sheet is compressed and the thickness of the tissue is increased until it intimately contacts the plates. The plates 703 may prevent the sheet 702 from overlapping on itself. The plates 703 may be placed around a specific region of the sheet 702 so as to increase the thickness of the sheet only in that specific region. The sheet 702 may also be stretched in other regions as described in the above embodiments, either after the sheet 702 has been compressed or at the same time it is being compressed.

Figure 8:
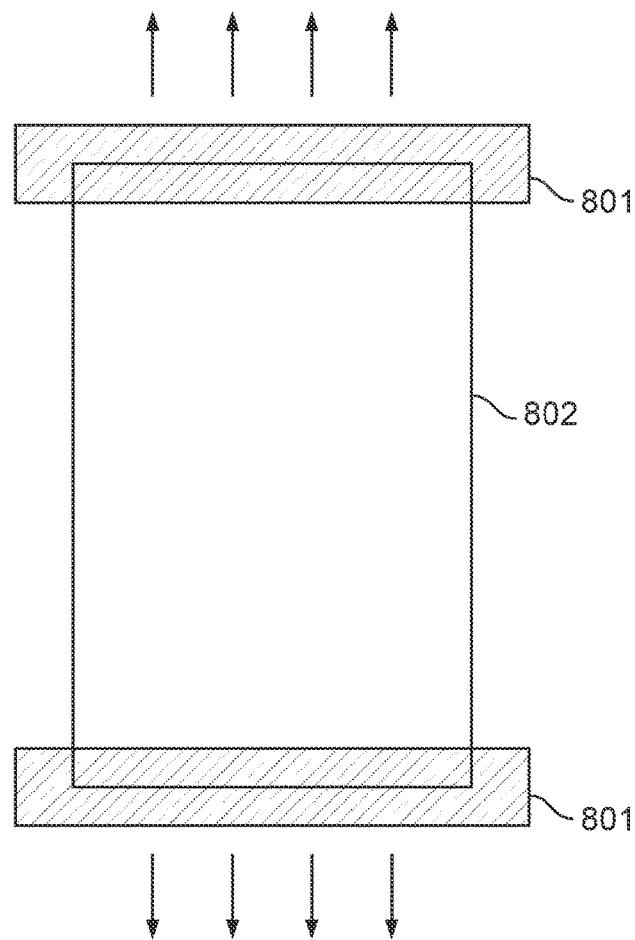
FIG. 8 is a highly schematic representation of a stretching technique according to yet another embodiment of the present disclosure.

FIG. 8 is an illustration of a sheet as described above being stretched. In this embodiment, the opposite ends of sheet 802 are held by clamps 801 which may be pulled in relative directions away from one another to stretch the sheet. A first end of the sheet 802 may be held fixed while the other end of the sheet is moved away from the first end, or both ends may be moved in directions away from one another. The ends of the sheet 802 may be moved by any mechanical apparatus capable of moving one end of the sheet away from a fixed end, or capable of moving both ends in directions away from one another. The mechanical means may include pulling the sheet 802 repeatedly using a cyclic motion. The mechanical apparatus for pulling the sheet 802 may include a linear actuator, tensile testing equipment or a rotating motor. The sheet 802 may be pulled using a cyclic motion for a varying number of cycles depending on the material of the sheet. The number of cycles may be between about 50 cycles and about 1500 cycles. The number of cycles may also be between about 75 cycles and about 1250 cycles, between about 100 cycles and about 1000 cycles, or between about 150 cycles and about 750 cycles. In another stretching technique, the sheet may be held vertically, with the top of the sheet attached to a frame and weights attached to the bottom of the sheet. The sheet 802 may be stretched by gravity pulling the weights. In either case, stretching the sheet reduces its thickness. The whole sheet 802 may be pulled to stretch out and reduce the thickness of the entire sheet or a portion of the sheet may be pulled to reduce the thickness in a select region of the sheet. If the whole sheet 802 is pulled, a thicker starting sheet may be used. The thickness of the whole sheet before being pulled may be between about 100 μm and about 2000 μm. After the sheet 802 has been pulled and stretched, the resulting thickness may be between about 25 μm and about 1000 μm, and may be above about 1000 μm depending on the number of cycles.

Figure 9:
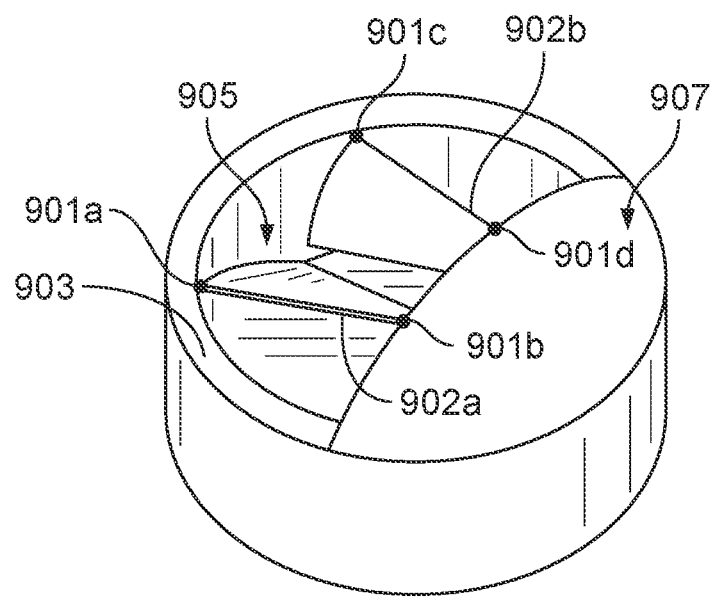
FIG. 9 is a highly schematic representation of a stretching technique according to a still further embodiment of the present disclosure.

FIG. 9 illustrates another technique for stretching any of the sheets described above. A fixture may be used to stretch the sheet (not shown), where the sheet may be attached to the bottom of frame 903. Frame 903 may have a generally round configuration formed from any rigid material, including metals and polymers. A portion 907 of the interior of the frame 903 may be filled with a solid material, leaving an open area 905 that is generally in the size and shape of a leaflet. One or more walls may be arranged within open area 905 and may extend from the top of frame 903 to about the bottom of the frame. In the embodiment of FIG. 9, two walls 902a, 902b are arranged in open area 905, although other embodiments may include only one such wall or more than two such walls. A first end of each wall 902a, 902b is connected to the outer circumference of frame 903 by a first pivot point 901a, 901c, respectively, and a second end of each wall is connected to the portion 907 of the frame by a second pivot point 901b, 901d, respectively. Pivot points 901a, 901b enable wall 902a to pivot about an axis that lies in a plane at the top of frame 903. Similarly, pivot points 901c, 901d enable wall 902b to pivot about a different axis that lies in the plane at the top of the frame 903. Walls 902a, 902b may be formed separately from frame 903, such as by molding, 3D printing or another technique, and may be subsequently attached to the frame. For example, walls 902a, 902b may be 3D printed and attached to frame 903 with a ball and socket connection, a pin or axle in aperture connection, or any other connection that enables the walls to pivot relative to the frame. Applying force to the sides of walls 902a, 902b may cause them to pivot at pivot points 901a, 901b and 901c, 901d, respectively.

The bottom surfaces of walls 902a, 902b may be flat, and may be parallel with the bottom of frame 903 or may be at an angle relative to the bottom of the frame. When angled, the angle may be parallel to the longitudinal axis of the wall from one pivot point to the other, or may be transverse to the longitudinal axis such that the length of the wall from top to bottom is greater at the end near one pivot point and lesser at the end near the other pivot point. Further, the length of walls 902a, 902b in the height direction may be about the same as the height of the frame 903 such that the bottom surfaces of the walls contact the sheet at the bottom of the frame without pivoting. In alternative embodiments, walls 902a, 902b may each be shorter or taller than the frame. When walls 902a, 902b are pivoted away from one another toward the circumference of frame 903, the bottom surfaces of the walls will contact the sheet, pulling portions of the sheet away from one another to stretch and thin the area of the sheet between the two walls. The amount of thinning will depend on the distance from the bottom surface of walls 902a, 902b in the rest position to the sheet, and the amount the walls are pivoted. The further the bottom surfaces of the walls in the rest position are from the sheet, the further the walls can be pivoted before they contact the sheet. As a result, pivoting of walls 902a, 902b after contact with the sheet will thin the sheet by a lesser amount than if the bottom surfaces of the walls contact the sheet in the rest position, in which case the thinning of the sheet would commence almost immediately upon pivoting of the walls.

Walls 902a, 902b may also create thinner regions of the sheet in another manner. Walls 902a, 902b may have a greater overall height than that of frame 903 such that the bottoms of the walls extend lower than the bottom surface of the frame. When that is the case, the bottom surfaces of the walls will contact the sheet before the bottom surface of frame 903 contacts the sheet. Applying a downward force on the top of frame 903 will drive walls 902a, 902b into the sheet, thinning the sheet in the shapes and positions of the walls until the bottom surface of frame 903 contacts the sheet. Thus, by controlling the distance between the bottom of frame 903 and the bottom surfaces of walls 902a, 902b, a desired amount of thinning of the sheet may be achieved in the regions of the sheet below the walls.

Walls 902a, 902b are shaped and positioned to create the preferred leaflet thickness profile and are placed within the open area 905 of frame 903 to achieve the preferred leaflet thickness profile of the sheet. For example, walls 902a, 902b may be positioned closer to one another to form a smaller central region of the leaflet, or walls 902a, 902b may have different heights so that when they pivot, they contact the sheet for different amounts of time, causing the sheet to stretch to greater or lesser degrees. The number of walls 902 within frame 903 may be varied based on the manufacturing process. Between about 2 walls and about 20 walls may be used as needed.

Figure 10:
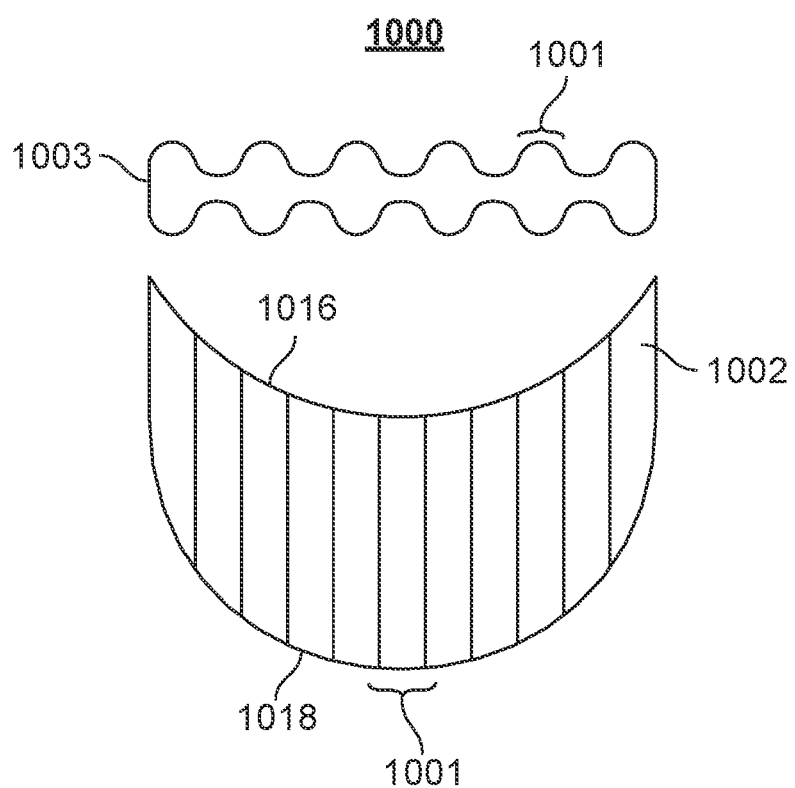
FIG. 10 is a plan view and a front elevational view of another embodiment of a leaflet of the present disclosure.

FIG. 10 shows an additional embodiment of a leaflet for use in a prosthetic heart valve. The leaflet 1000 may be in the form of a sheet material 1002 having a multiplicity of ribs 1001 extending from free edge 1016 to sewing edge 1018. The ribs 1001 may be formed by one of the various stretching and/or compressing techniques described above. For example, as shown in FIG. 7, the sheet 1002 may be compressed to form ribs 1001 having a thickness of between about 100 μm and about 500 μm using clips 701 and plates 703. Plates 703 may include the rib shapes defined in their surfaces, such as in the form of undulations. Thus, when the sheet 1002 is placed between the plates 703 and compressed as described above, the undulations may form ribs 1001 in the sheet. As can be seen in the cross-section 1003 of the leaflet 1000, ribs 1001 may form peaks and valleys throughout the sheet 1002. The ribs 1001 may be formed across the entire leaflet or only in the thicker regions of the leaflet, near the sewing edge 1018. The leaflet 1000 may be attached to the frame or stent of a prosthetic heart valve through the ribs 1001. Thus, when ribs 1001 are formed in the thicker regions of the leaflet, the leaflet attachment to the stent of a collapsible valve will be through a material, but only a minimum amount of material will be thickened while the rest of the leaflet is thinner to allow for a smaller transcatheter delivery profile. When ribs 1001 are formed across the entire leaflet 1000, the leaflet may be stronger and more flexible in one direction, similar to native leaflets.

Figure 11:
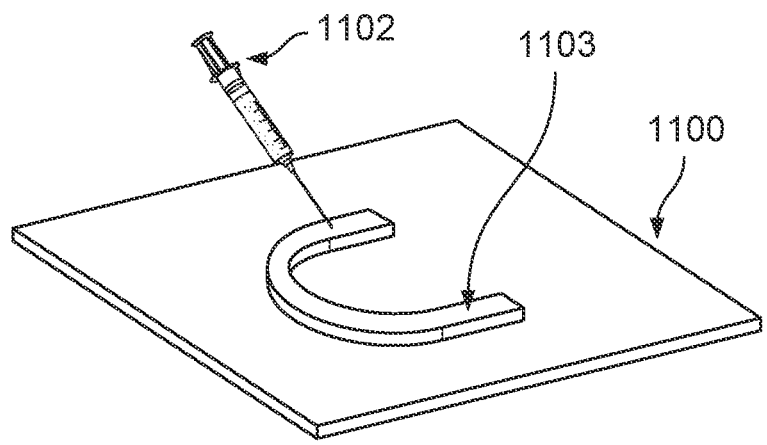
FIG. 11 is a perspective view showing a method for incorporating cellular material in tissue.

FIG. 11 shows an additional embodiment in which cellular material may be incorporated into any of the leaflets described above in order to increase the strength in a region or regions of the leaflet. The leaflet may be composed of a sheet of tissue 1100. The tissue 1100 may be a bovine tissue or other tissue known in the art. The tissue 1100 may include a region 1103 or multiple regions 1103 that may be injected with collagen-producing cells 1102. The amount of collagen produced in the collagen-producing cells 1102 depends on how long the tissue is incubated. The longer the tissue 1100 is incubated, the more collagen will be produced. Depending on the incubation time, the amount of collagen may increase in the regions 1103 by between about 5% and about 30%. The region or regions 1103 may correspond to the belly or sewing edge of the leaflet to be fabricated. The collagen-producing cells may be smooth muscle cells, fibroblasts or stem cells. The tissue 1100 may be injected with collagen-producing cells before fixation. After the cells 1102 have been injected into the tissue 1100, the tissue may be incubated with a cellular growth medium to allow the cells to produce collagen, increasing the density and strength of the tissue in the injected region or regions 1103. The density and strength of the tissue may be increased by between about 5% and about 30%. Any cellular growth medium known in the art may be used, with or without the presence of specific growth factors to drive collagen production. For example, the cellular growth medium may be Dulbecco's modified eagles medium along with fetal bovine serum and growth factors such as TGF-beta and vitamin C, etc. Also, an alternate serum may be used with the Dulbecco's modified eagles medium. After the cells have grown, the tissue 1100 may be fixed.

In an additional embodiment, the regions 1103 of the tissue 1100 may be injected with a flexible polymer. The flexible polymer may be silicone or urethane, and may include collagen-producing cells. The collagen-producing cells may be smooth muscle cells, fibroblasts or stem cells. In one embodiment, the tissue 1100 may be injected with a solution of liquid silicone and collagen-producing cells before the solution solidifies.

Figure 12A:
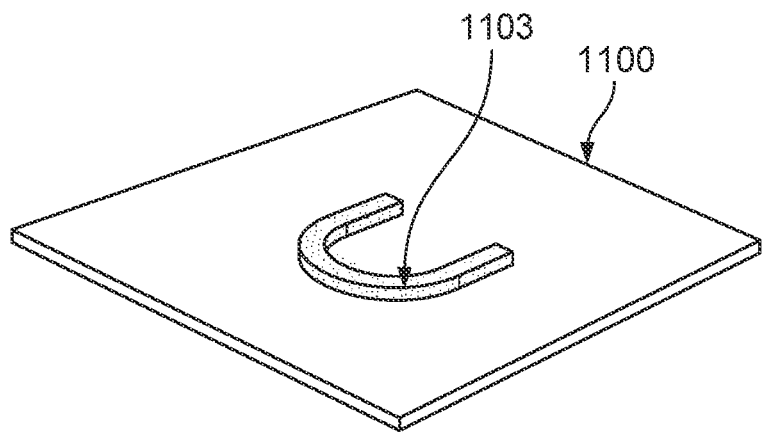
FIG. 12A is a perspective view showing the tissue of FIG. 11 with cellular material incorporated therein.
Figure 12B:
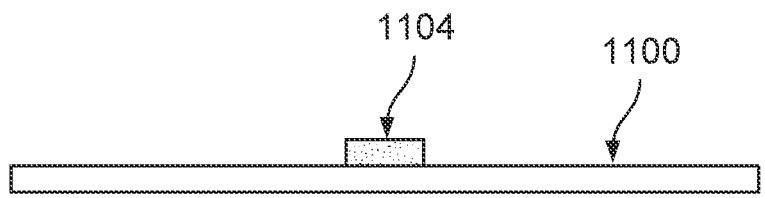
FIG. 12B is a side elevational view of the tissue of FIG. 11 with cellular material incorporated therein.

FIGS. 12A and 12B show still another embodiment in which cellular material is incorporated into the leaflets. The cellular material may be collagen-producing cells, for example, fibroblasts, smooth muscle cells and stem cells; Glycosaminoglycans (GAGs), elastin, or a combination thereof. The tissue 1100 may include a region or multiple regions 1103 that incorporate the cellular material. The cellular material may be mixed with a hydrogel to form a solution which entraps the hydrogel. The hydrogel may be a collagen, fibrin or synthetic polymer hydrogel. The solution may be placed in a layer 1104 on the region 1103 of the tissue 1100, as can be seen in FIG. 12B. The hydrogel layer 1104 may have a thickness of between about 1 mm and about 10 mm, or between about 1 mm and about 5 mm. The tissue 1100 may be incubated with a cellular growth medium to produce collagen. The cellular growth medium may be any cellular growth medium known in the art, with or without the presence of specific growth factors to drive collagen production. The collagen produced by the cellular material in the hydrogel may help the tissue adhere to the pericardium along the belly or sewing edge of the leaflet. After incubation, the tissue may be fixed. If the patient's own cells are used in the cellular material that is incorporated into the tissue 1100, fixation may not be required because the tissue would be autologous. Alternatively, after incubation the cells may be removed through decellurization to render the tissue inert without fixation. Allogenic cells, or cells of the same species as the tissue, may also be used in the cellular material. These cells would be undergo either decellularization or fixation to make the tissue 1100 immunologically compatible.

To summarize the foregoing, one embodiment of the disclosure provides a prosthetic heart valve, including a support structure; and a valve assembly disposed within the support structure, the valve assembly including a plurality of leaflets, each of the leaflets being formed from a sheet of tissue and having a sewing edge, a free edge, and a non-uniform thickness; and/or each of the leaflets has a plurality of regions, and each of the regions may have a different thickness; and/or the thickness of a first region of the leaflet may be between about 5% and about 20% less than the thickness of a second region of the leaflet; and/or the sewing edge may have a thickness between about 10% and about 20% greater than a thickness of the free edge; and/or the thickness of the leaflet may be greater at the sewing edge and may gradually decrease toward the free edge; and/or the thickness of the leaflet may decrease with a smooth transition from the sewing edge to the free edge; and/or the thickness of the leaflet may decrease with a stepped transition from the sewing edge to the free edge; and/or collagen-producing cells may be incorporated into the tissue; and/or the collagen-producing cells may be smooth-muscle cells, fibroblasts or stem cells; and/or the collagen-producing cells may be incubated on the tissue so as to produce collagen on the tissue.

Another embodiment of the disclosure provides a method for fabricating a leaflet for a prosthetic heart valve, the leaflet having a non-uniform thickness, the method including providing a sheet of a leaflet material, the sheet having a first thickness; attaching the sheet to a frame; and moving a first probe into contact with a surface of the sheet, whereupon the probe exerts a force in a region of the sheet to change the thickness of the region of the sheet to a second thickness different from the first thickness; and/or the second thickness may be less than the first thickness; and/or the first thickness may be about 100 µm and the second thickness may be about 75 µm; and/or the moving step may move the first probe into contact with a top surface of the sheet, and the method may further include moving a second probe into contact with a bottom surface of the sheet, whereupon the first probe and the second probe may exert a compressive force on the region of the sheet, compressing the sheet to decrease the thickness of the region; and/or a plurality of ribs may be formed throughout the sheet; and/or the leaflet material may be tissue; and/or the method may further include fixing the tissue with glutaraldehyde.

A further embodiment of the disclosure provides a method for fabricating a leaflet for a prosthetic heart valve, the method including layering a sheet of a leaflet material over a first mold portion having a first leaflet form, the sheet having a uniform thickness; and applying a second mold portion to the sheet, the second mold portion having a second leaflet form different from the first leaflet form, wherein the second mold portion pushes the sheet against the first leaflet form to form the sheet into a sheet having a non-uniform thickness; and/or the leaflet material may be tissue; and/or the method may further include fixing the tissue with glutaraldehyde.

A still further embodiment of the disclosure provides a method for fabricating a leaflet for a prosthetic heart valve, the method including providing a sheet having a first major surface, a second major surface, and a first thickness between the first major surface and the second major surface; positioning a first plate adjacent to the first major surface and a second plate adjacent to the second major surface so that a distance between the first plate and the second plate defines a desired sheet thickness greater than the first thickness; and moving opposed edges of the sheet toward one another between the first plate and the second plate to force the sheet against the first plate and the second plate to increase the thickness of the sheet to the desired thickness; and/or the first plate and the second plate may be parallel; and/or the first plate may have a first edge and a second edge opposite the first edge and the second plate may have a first plate edge and a second plate edge opposite the first plate edge, the first plate and the second plate may not be parallel, and the distance between the first edge of the first plate and the first plate edge of the second plate may be less than the distance between the second edge of the first plate and the second plate edge of the second plate.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A method for fabricating a leaflet for a prosthetic heart valve, the leaflet having a non-uniform thickness, the method comprising:

providing a sheet of a leaflet material, the sheet having a first thickness;

attaching the sheet to a frame; and moving a first probe into contact with a surface of the sheet, whereupon the probe exerts a force against a region of the sheet to compress or stretch the region of the sheet and thereby change the thickness of the region of the sheet to a second thickness different from the first thickness.

2. The method of claim 1, wherein the second thickness is less than the first thickness.

3. The method of claim 1, wherein the first thickness is about 100 μm and the second thickness is about 75 μm.

4. The method of claim 1, wherein the moving step moves the first probe into contact with a top surface of the sheet, the method further comprising moving a second probe into contact with a bottom surface of the sheet, whereupon the first probe and the second probe collectively exert a compressive force on the region of the sheet, compressing the sheet to decrease the thickness of the region.

5. The method of claim 1, wherein a plurality of ribs is formed throughout the sheet.

6. The method of claim 1, wherein the leaflet material is tissue.

7. The method of claim 6, further comprising fixing the tissue with glutaraldehyde.

8. The method of claim 1, wherein the pressure force applied to the sheet stretches the sheet to reduce the thickness of the region of the sheet to the second thickness.

\* \* \* \* \*